United States Patent [19]

Smith, deceased et al.

[11] 4,029,809

[45] June 14, 1977

[54] METHOD OF PROTECTING PLANTS FROM PATHOGENS WITH CYANOMETHYL ARYL SULFONATES

[75] Inventors: Herbert Q. Smith, deceased, late of Malvern, Pa.; by Jacqueline Smith, legal representative, Yardley; Sameeh Said Toukan, Phoenixville, both of Pa.

[73] Assignee: Pennwalt Corporation, Philadelphia, Pa.

[22] Filed: July 25, 1975

[21] Appl. No.: 599,280

Related U.S. Application Data

[62] Division of Ser. No. 385,495, Aug. 3, 1973, Pat. No. 3,903,298.

[52] U.S. Cl. .......................... 424/275; 260/329 S; 260/332.2 C; 260/332.2 R; 260/332.3 R; 260/332.5
[51] Int. Cl.² ............................................ A01N 9/12
[58] Field of Search ..................................... 424/275

[56] References Cited

UNITED STATES PATENTS 3,536,721  10/1970  Soong et al. .............. 260/293.58 X
3,753,999  8/1973   Tempel et al. ................. 424/275 X

OTHER PUBLICATIONS

Cox et al., Chem Abst., vol. 72, (1970), 78,673c.
Lichtenberger et al., Chem. Abst., vol. 43, (1949), 294-2.

Primary Examiner—Allen J. Robinson

[57] ABSTRACT

Fungi or bacteria pathogenic to plants are inhibited by applying to the locus to be protected therefrom a biocidally effective amount of a cyanomethyl arylsulfonate represented by the formula $RSO_3CH_2CN$ where R is

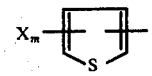

2 Claims, No Drawings

METHOD OF PROTECTING PLANTS FROM PATHOGENS WITH CYANOMETHYL ARYL SULFONATES

This is a division of application Ser. No. 385,495 filed Aug. 3, 1973 now U.S. Pat. No. 3,903,298.

This invention concerns a method of protecting plants from pathogens and plant diseases by treatment of the locus to be protected with a cyanomethyl arylsulfonate.

Many of the organisms that inhabit the soil subsist on living plants and may injure the roots and other undergrund portions, other may attack the crown of the plant, while still others are capable of damaging the stem and other above-ground portions of the plant. Fungi, bacteria and like plant pathogens attack a broad spectrum of plants including field crops, truck crops, cereals and grasses, and ornamental and house plants, including corn, soybeans, cotton, beets, sugar beets, oats, peanuts, onions, alfalfa, apples, peaches, beans, lettuce, celery, potatoes and others. The seriousness of the problem is enhanced when plants are grown year after year in the soil because the ready food supply nourishes the pathogens.

Cyanomethyl benzenesulfonate and cyanomethyl toluenesulfonate are known compounds: see "Preparation and Reactions of α-Cyanoalkyl Benzenesulfonates," H. W. Turner, Univ. Microfilms, Pub. No. 3082 (1952) Chem. Abs. 47, 2726a); J. Lichtenberger and C. Faure, Bull Soc. Chim. France 1948, pp. 995–1001 (Chem. Abs. 43, 2941i). Neither reference suggests that cyanomethyl benzenesulfonates might have activity against plant pathogens.

In accordance with this invention a cyanomethyl arylsulfonate is applied to the locus to be protected (i.e., the soil, a seedling, plant, or plant part) in sufficient amount to kill or otherwise effectively inhibit the development of soil and other fungi and bacteria pathogenic to plants. The cyanomethyl arylsulfonate useful in the process of this invention is represented by the formula $RSO_3CH_2CN$ where R is selected from the group consisting of

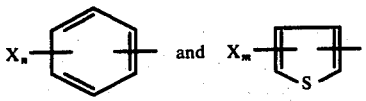

where X is independently hydrogen, halogen (i.e., chlorine, bromine, iodine or fluorine), alkyl or alkoxy (e.g., having from 1 to 18 carbon atoms, preferably 1 to 4, i.e., lower alkyl and lower alkoxyl, $NO_2$, CN, $CF_3$, $CONH_2$, $SO_2NH_2$, $H_2NCOO$, COOH, $YSO_2$ or OOCY, where Y is lower alkyl, $n$ is an integer of 1 to 5 and $m$ is an integer of 1 to 3. The preferred compounds are those of the above formulae wherein X is hydrogen, halogen, lower alkyl or nitro.

The cyanomethyl arylsulfonates embodied herein are generally effective as fungicides and bactericides while being minimally phytotoxic to the plants sought to be protected using biocidally effective dosages. In general, application in the range of from about 0.1 pound to about 20 pounds of the active agent per acre of surface treated gives effetive control of the pathogen. Although a smaller range of about 0.1 to about 5lbs./acre is obviously preferred, the optimum amount will depend upon environmental factors, including the specific compound used, soil type, method of application climatic conditions, crop response, stage of plant development at time of treatment, etc. The optimum dosage in a specific treatment can be readily determined by one having ordinary skill in the art. The compounds are generally effective against most of the more prominent genera of plant pathogens, including species of *Rhizoctonia, Pythium, Fusarium, Verticillium, Sclerotinia, Aphanomyces, Asocochyta, Phytophthora, Thielaviopsis, Monilinia, Alternaria, Glomerella, Xanthomonas, Abrugo candida, Aspergillus, Botrytis, Cerospora, Cladosporium, Erysiphe, Fusicladium, Helminthosporium, Penicillum, Plasmopara, Septoria* and *Taphrina*.

The cyanomethyl arylsulfonates are liquids or crystalline solids which are insoluble in water, but are very soluble in a variety of typical solvents, for example, acetone, diacetone alcohol, dimethylformamide, xylene, isopropanol, ethanol, methanol, benzene, methyl chloroform and others. The agent may be formulated for application in the field as dispersions or solutions in organic solvents or emulsifiable oils. To prepare the dispersion a suitable wetting agent may be added which aids in the preparation of the formulation and which also serves to help penetration of the compound into soil and plant surfaces. Suitable dispersion concentrates may be prepared with or without suspending agents by ball milling or other fine grinding techniques. Suspending agents will be selected from the various agents readily available, such as lignin sulfonates, bentonite, dilute solutions of "Methocel" cellulose derivative, and the like. Formulations may also be prepared as emulsion concentrates for dilution with water for field applications. These may be prepared by the use of suitable solvents such as xylene, heavy aromatic naphtha, isophorone, benzene, heptane, heavy mineral oils, kerosene, and other solvents immiscible with water, with the addition of a suitable anionic, cationic, or nonionic emulsifying agent such as long-chain alkyl benzenesulfonates or polyglycol ethers. In lieu of said dispersion or oil-in-water emulsion, the compounds may be prepared and applied merely as a solution in an organic solvent, such as those solvents mentioned above, or in such water-miscible solvents as diacetone alcohol, acetone, dimethyl sulfoxide, dimethylformamide, phosphoric acid esters, etc. The latter solutions can also be diluted with water to the desired concentrations. The compounds are preferably applied as formulations of wettable powders which are prepared by direct grinding of the compound with a blend of suitable carrying agent such as attapulgite, bentonite, kieselguhr and the like. It is desirable to grind such a blend in a hammer mill so that 99% will pass through a 325 mesh screen. Wettable powders may also be prepared by absorbing a solution of the compound in a solvent such as xylene or acetone on a powdered clay as attapulgite or diatomaceous earth. All wettable powder preparations may contain a dispersing agent such as a lignin sulfonate and a wetting agent such as an alkylaryl polyether glycol. The concentration of the active agent will, in general, range from about 0.01% to about 75% by weight of the total formulation, i.e., of the combined weight of the active agent and the carrier medium, whether liquid or/and powder. The techniques of preparing pesticidal formulations by compounding carriers with the active agent are well known to those acquainted with the art.

While a preferred method of utilizing the agents is to apply the formulation to the soil to prevent infection of seedlings by the pathogenic organisms, other methods such as "hopper box" and "furrow" treatments can be used to achieve essentially the same results, wherein, for example, the formulation is contacted with the seed in the hopper box of the planting apparatus prior to the planting operation. These methods also eliminate any organisms borne on the seed itself.

The cyanomethyl arylsulfonates are conveniently prepared by reacting substantially equimolar amounts of glycolonitrile and the appropriate arylsulfonyl chloride precursor, at a temperature ranging from about 0° to 100° C., preferably 0° to 25° C. The products are liquids at room temperature or solids which melt at rather moderate temperatures. Illustrative procedures for preparing representative species of the cyanomethyl arylsulfonates embodied herein are next presented. All structures of synthesized compounds were confirmed by elemental analyses and infrared spectra.

EXAMPLE 1

Cyanomethyl benzenesulfonate

A pale, straw-colored oily liquid, $n_D^{20}$ 1.5231

EXAMPLE 2

Cyanomethyl p-toluenesulfonate

Method of preparation: 8.1 g (0.1 mole of glycolonitrile (70% aqueous solution) is added to a cooled (15°–20° C.) mixture of 9.5 g (0.05 mole) of p-toluenesulfonyl chloride in 20 ml. of 1,2-dimethoxyethane and 50 ml. distilled water. A solution of 2.1 g (0.05 mole) of NaOH in 50 ml. distilled water is added slowly with stirring at 20°–25° C. over a period of 6.5 hours, maintaining the pH of the reaction mixture at about 8. The insoluble material is filtered off, washed with cold water, and dried at 40° C. under vacuum to yield 6.8 g (64% conversion) of the product, a light brown solid, m.p. 48°–50.5° C.

EXAMPLE 3

Cyanomethyl 2-thiophenesulfonate

Method of preparation: Glycolonitrile is reacted with 2-thiophenesulfonyl chloride using the procedure as described in the previous example, with 2 hours of reaction at 0° C., followed by three hours at room temperature. The reaction mixture separates into two layers; the bottom dark layer is isolated and dissolved in diethyl ether, the solution washed with weak caustic solution and cold water, and the solvent is stripped off under reduced pressure to give the product (in 79% conversion), a green oily liquid, $n_D^{24.5}$ 1.535.

EXAMPLE 4

Cyanomethyl m-nitrobenzenesulfonate

Preparation: The technique of Example 2 is used to react glycolonitrile with m-nitrobenzenesulfonyl chloride. The product is recovered from the reaction mixture by filtration and recrystallized from ethanol. The dried product (45% conversion) is an amber solid, m.p. 66°–69° C.

EXAMPLE 5

Cyanomethyl p-fluorobenzenesulfonate, obtained in 87% conversion from the reaction of p-fluorobenzenesulfonyl chloride with glycolonitrile according to the procedure of Example 3. The product is a light pinkish liquid $n_D^{24}$ 1.5082.

EXAMPLE 6

Cyanomethyl p-bromobenzenesulfonate, obtained in 44% conversion from the reaction of p-bromobenzenesulfonyl chloride with glycolonitrile according to the procedure of Example 4. The product is a white solid, m.p. 57°–59° C.

EXAMPLE 7

The iodo analog, cyanomethyl p-iodobenzenesulfonate, a white solid, m.p. 87°–90° C., is similarly prepared (in 73% conversion) by reacting glycolonitrile with p-iodobenzenesulfonyl chloride.

EXAMPLE 8

Cyanomethyl p-chlorobenzenesulfonate, obtained in 51% conversion from the reaction of p-chlorobenzenesulfonyl chloride with glycolonitrile according to the procedure of Example 3. The product is a colorless liquid $n_D^{24}$ 1.5442.

EXAMPLE 9

Cyanomethyl 3,4-dichlorobenzenesulfonate, obtained in 88% conversion from the reaction of 3,4-dichlorobenzenesulfonyl chloride with glycolonitrile according to the procedure of Example 3. The product is recovered as a slightly pinkish, viscous liquid which, on standing at room temperature, crystallizes out as a light pink solid, m.p. 46°–49° C.

EXAMPLE 10

Cyanomethyl 2,4,5-trichlorobenzenesulfonate, obtained in 65% conversion from the reaction of 2,4,5-trichlorobenzenesulfonyl chloride with glycolonitrile according to the procedure of Example 4. The product is a white solid, m.p. 80°–83° C.

EXAMPLE 11

Cyanomethyl 2,4-dinitrobenzenesulfonate, obtained in 77% conversion from the reaction of 2,4-dinitrobenzenesulfonyl chloride with glycolonitrile. The product is a light yellow solid, m.p. 72°–75° C.

EXAMPLE 12

Cyanomethyl pentachlorobenzenesulfonate, obtained in 63% conversion from the reaction of pentachlorobenzenesulfonyl chloride with glycolonitrile. The product is a white solid, m.p. 130°–134° C. (incomplete).

The efficacy of the cyanomethyl arylsulfonates in controlling plant pathogens is confirmed by standard tests known as the "Spore Germination" test and the "Bactericide - Primary" test. The Spore Germination test is a laboratory test conducted in concavities in a glass slide in which seven day old potato dextrose agar cultures of the spores *Monilinia fructicola*, *Alternaria brassicola*, and *Glomerella cingulata* are treated with 1,000, 100, 10, and 1 ppm of the test agent. The formulated chemical (10% concentration in xylene) is serially diluted with distilled water to obtain concentrations of 2,000, 200, 20, and 2 ppm. One drop of the 2 ppm concentration is placed in each of the first three concavities in the slide and then one drop of the 20 ppm concentration is placed in each of the next three concavities and the same is done for the 200 and 2,000 ppm concentrations.

The slides are kept at room temperature for 24 hours to allow the chemical solution in the concavities to dry. Spores are now washed from the surface of the agar cultures with distilled water containing 0.1% dextrose. Each spore suspension is filtered through four layers of cheesecloth and diluted with additional dextrose water to obtain 50,000 spores per ml. Two drops of a spore suspension of one of the organisms is added to each of the four concavities containing the four dried dilutions of the test chemical. The same is done with the two remaining organisms and the eight remaining concavities on the slide. Ten ml. of distilled water is added to the filter paper in each plate and a glass support rod laid on top of the paper. An agglutination slide is placed on the rod and the dish cover put in place.

The plates are incubated at 18° to 20° C. for 24 hours, and the slides are observed under the microscope and germination or no germination recorded for each chemical concentration.

The rating of an agent run through the spore germination screen is assigned as follows;

| Concentration, ppm | Germination | Rating |
|---|---|---|
| 1,000 | Yes | 0 |
| 1,000 | No | 1 |
| 100 | Yes | 1 |
| 100 | No | 2 |
| 10 | Yes | 2 |
| 10 | No | 3 |
| 1 | Yes | 3 |
| 1 | No | 3 |

The "Bactericide Test" is conducted with treated assay dishes and seeded agar plates, wherein the formulated chemical (10% concentration in xylene) is serially diluted with distilled water in two tubes to obtain concentrations of 2,000 and 200 ppm. Usually the first two concentrations obtained in the spore germination test are used as the two tests and conducted at the same time. Assay disks are dip treated and the disks are allowed to dry for 24 hours.

A bacterial suspension (*Xanthomonas pruni*) is made by washing a 24 hour old nutrient agar slant culture with 5 ml. of sterile, distilled water. 2 ml. of this suspension is added to 125 ml. of warm, melted nutrient agar in a flask. The seeded agar is then poured into ten 100 × 15 mm. Petri plates. After the seeded agar has solidified and cooled, the treated disks are placed on the surface. Four disks, representing two rates of two test chemicals, are placed in each dish. After 24 hours the plates are observed and the diameter of the zone of inhibition, including disk, is recorded. The rating of an agent run through the bacterial assay disk screen is assisgned as follows:

| Concentration, ppm | Zone of Inhibition | Rating |
|---|---|---|
| 2,000 | None or much less than standard | 0 |
| 2,000 | Slightly less or greater than standard | 1 |
| 200 | Some but much less than standard | 2 |
| 200 | Slightly less or greater than standard | 3 |
| Standard | 21.2% streptomycin sulfate | |

The results of the screening tests on the above representative cyanomethyl arylsulfonates are as follows:

| Example No. | Spore Germination Rating | Bactericide Rating |
|---|---|---|
| 1 | 3 | 1 |
| 2 | 3 | 1 |
| 3 | 3 | 3 |
| 4 | 3 | 1 |
| 5 | 3 & 1* | 3 |
| 6 | 2 | 3 |
| 7 | 3 | 3 |
| 8 | 2 | 3 |
| 9 | 0 | 3 |
| 10 | 3 | 1 |
| 11 | 3 | 0 |
| 12 | 3 | 0 |

*3 on Alternaria 1 on Monilia and Glomerella

In another test, the soil fungicide effectiveness of representative compounds is determined by treating seeds of sugar beet, cucumber and cotton with a dry clay carrier formulation of the material, and mixing the formulation with soil infested with Pythium sp. at rates of 5, 15, and 50 lb./acre. of total active ingredient (including that retained by the seeds.) The percentage control of the soil organism is determined from the number of emerged healthy seedlings compared to that of the untreated check sample. Control of the fungus at 5 lb./acre indicates excellent soil fungicidal properties. Referring to representative compounds screened, those labeled above as Examples 3 and 5 show excellent results in inhibiting such organism growth, Examples 2 and 9 give good results, and Examples 1 and 4 give fair results. Other compounds are not especially effective in inhibiting this particular organism.

We claim:
1. A method of inhibiting fungi or bacteria pathogenic to plants which comprises applying to said fungi, bacteria or the locus thereof a biocidally effective amount within the range of about 0.1 pound to about 20 pounds per acre of a cyanomethyl arylsulfonate represented by the formula $RSO_3CH_2CN$ where R is

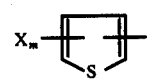

wherein X is selected from the group consisting of halogen, alkyl having from 1 to 18 carbon atoms, alkoxy having from 1 to 18 carbon atoms, $NO_2$, CN, $CF_3$, $CONH_2$, $SO_2NH_2$, $H_2NCOO$, COOH, $YSO_2$ and OOCY, wherein Y is lower alkyl, and $m$ is 0 or an integer of 1 to 3.

2. The method according to claim 1 wherein $m$ is 0.

* * * * *